United States Patent [19]

Robins

[11] Patent Number: 4,809,748
[45] Date of Patent: Mar. 7, 1989

[54] AUTOMATIC SAMPLING DEVICE

[75] Inventor: David G. Robins, Stockport, England

[73] Assignee: Ciba-Geigy Corporation, Ardsley, N.Y.

[21] Appl. No.: 568,780

[22] Filed: Jan. 6, 1984

[30] Foreign Application Priority Data

Jan. 13, 1983 [GB] United Kingdom ................. 8300883

[51] Int. Cl.⁴ ............................................. F16K 31/04
[52] U.S. Cl. ............................. 137/625.11; 251/129.13
[58] Field of Search ....................... 137/625.11, 624.11, 137/554, 555; 251/133, 134, 136

[56] References Cited

U.S. PATENT DOCUMENTS

| | | | |
|---|---|---|---|
| 2,573,297 | 10/1951 | Atkinson | 251/136 |
| 3,000,398 | 9/1961 | Link | 137/625.11 |
| 3,008,490 | 11/1961 | Angelos | 137/625.11 |
| 3,914,676 | 10/1975 | Madonian et al. | 251/134 |
| 4,139,355 | 2/1979 | Turner et al. | 251/134 |
| 4,156,437 | 5/1979 | Chivens et al. | 137/554 |
| 4,185,770 | 1/1980 | Nagel | 251/136 |
| 4,299,251 | 11/1981 | Dugas | 137/555 |
| 4,310,022 | 1/1982 | Cohen | 137/625.11 |
| 4,350,429 | 9/1982 | Slavin | 137/625.11 |
| 4,428,511 | 1/1984 | Howell | 137/625.11 |

FOREIGN PATENT DOCUMENTS

| | | |
|---|---|---|
| 860257 | 2/1961 | United Kingdom . |
| 1075803 | 7/1967 | United Kingdom . |
| 1118926 | 7/1968 | United Kingdom . |
| 1272364 | 4/1972 | United Kingdom . |
| 1363922 | 8/1974 | United Kingdom . |
| 1399242 | 6/1975 | United Kingdom . |
| 1571322 | 7/1980 | United Kingdom . |
| 2039079 | 7/1980 | United Kingdom . |
| 1574319 | 9/1980 | United Kingdom . |

Primary Examiner—John Rivell
Attorney, Agent, or Firm—Harry Falber

[57] ABSTRACT

The invention provides a multiposition rotary liquid sampling valve wherein a plurality of inlets are linked one at a time to a common outlet via a rotor, which comprises an electric motor for turning the rotor, means for applying power to the motor, means for sensing the position of the rotor and means, connected to the sensing means, for immediately stopping the motor when the rotor reaches a desired position by disconnecting the power applied to the motor and simultaneously applying a braking action to the motor.

6 Claims, 2 Drawing Sheets

AUTOMATIC SAMPLING DEVICE

The present invention relates to a multi-position rotary liquid sampling valve.

Multi-position rotary valves are well known articles by which samples of a number of liquids can be obtained separately and, for instance passed to an automatic analyser. One use of these valves is to measure the rate of dissolution of tablets or pills having different formulations.

The rotary valves comprise a plurality of inlets and a single central outlet, arranged so that the outlet can be connected to any one of the inlets separately. This is achieved by connecting the inlets and outlets to a series of holes bored through a stator abutting the face of which is a rotor having two interconnected holes one of which is in permanent contact with the outlet and the other of which can be moved to contact any one of the inlets by turning the rotor.

The rotor is normally turned manually or by pneumatic means. When operated manually the positions whereby one of the inlets is aligned with the hole in the rotor is indicated by a small but noticeable increase in the resistance to rotation. This is usually effected by fixing a hub to the rotor and having a series of detents in the outer surface of the hub, the number corresponding to the number of inlets. Around the hub are arranged one or two more balls and springs so that the balls are forced into the detents by the springs when the detents reach the desired position. This causes a resistance to the rotation and indicates correct alignment.

When operated pneumatically a double acting pneumatic cylinder and lever is used to convert reciprocal piston movement to rotary movement. A ratchet mechanism is used to rotate the rotor the desired distance, for each movement of the piston.

The main disadvantage of the manual system is that the device needs constant attention and the timing of the sampling is not always as accurate as is desired. A disadvantage of the pneumatic system is that a source of compressed gas or air is required and either a further device is needed to actuate the piston at the desired time or it must be done manually.

Automatic operation of the valve by a wholly electrical system is desirable as accurate timing can be arranged. However to date this has not been achieved because of the necessity of ensuring accurate alignment of the inlet hole in the rotor with a desired inlet hole in the stator. Any slight misalignment can prevent any sample being taken at all.

We have now developed a device whereby the rotor is moved automatically by an electric motor and stops when the inlet holes are correctly aligned without overshooting.

Accordingly, the present invention provides a multi-position rotary liquid sampling valve wherein a plurality of inlets are linked one at a time to a common outlet via a rotor, which comprises an electric motor for turning the rotor, means for applying power to the motor, means for sensing the position of the rotor and means, connected to the sensing means, for immediately stopping the motor when the rotor reaches a desired position by disconnecting the power applied to the motor and simultaneously applying a braking action to the motor.

The motor preferably drives the rotor via step-down gearing so that the rotor turns at a considerably slower speed than the speed of the motor. A suitable speed for the rotor is about 5 rpm, and this helps to prevent any overshooting of the desired position.

The means for applying power to the motor preferably comprises a timing means or programming device, which switches on the power to the motor at predetermined intervals. As soon as the motor starts, the rotor is moved from its previous position and the position sensing means allows the rotor to continue to turn until it reaches the next desired position.

Various sensing means may be used to sense the position of the rotor. One means is to replace one spring and ball combination on the manual version of the valve and insert a probe which is connected to a microswitch. When the rotor is turning the switch is depressed allowing the motor ot continue. As soon as a detent position is reached, the probe switches off the microswitch and thus the power supply to the motor is disconnected.

Another means is to fit a cam shaft coaxially with the motor drive shaft and rotor which may be connected to a microswitch as above.

Another means is a photoelectric cell and a light source on opposite sides of the shaft with means on the shaft or rotor for interrupting the light at some positions and allowing light to pass at other positions thereby switching the photoelectric cell on and off as desired.

The means connected to the sensing means for applying a braking action to the motor to ensure immediate stopping may be, e.g. a DC braking circuit or a device which actuates a brake on to the rotor of the motor.

As the valve can easily be set to operate automatically it may not be possible to easily ascertain which inlet is connected to the outlet at any one time. A visual indication may be incorporated e.g. by fixing a disc to the shaft of the motor having numbers around its circumference corresponding to the number of inlets. This would then rotate with the rotor and a fixed pointer or other indicator may be mounted on the valve associated with the numbers to indicate the position of the rotor and hence which inlet is connected to the outlet.

The invention is illustrated by way of Example with reference to the accompanying drawings in which.

Figure 1:
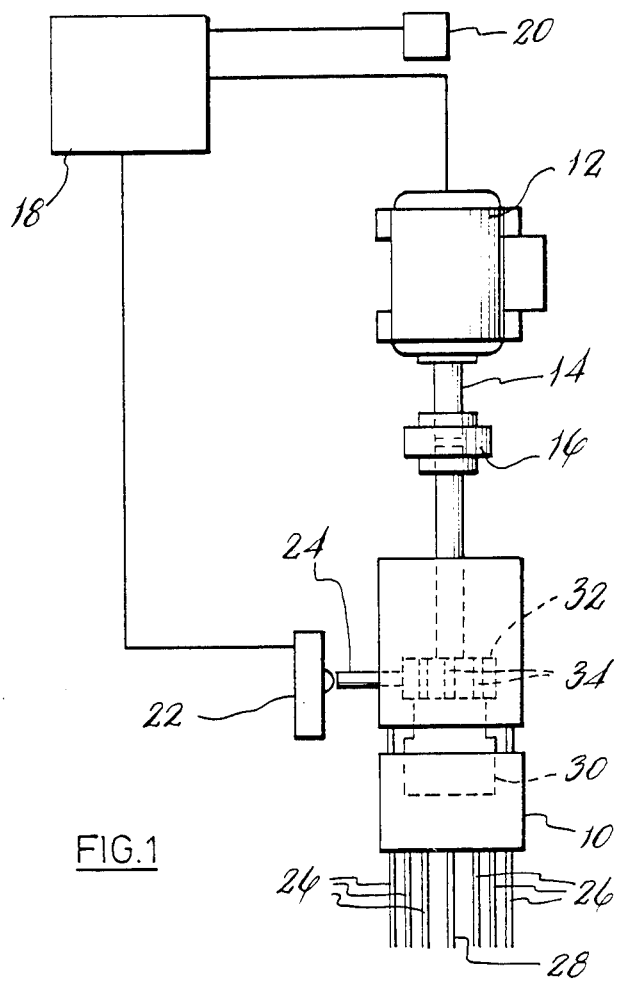
FIG. 1 is a block diagram of a sampling valve of the invention.

Referring to the drawings, multi-position liquid sampling valve 10 is connected to motor 12 via drive shaft 14 and shaft coupling 16. Motor 12 is controlled by motor control circuit 18 to which are connected start switch 20 and micro-switch 22 which is operated by valve position sensor 24 Valve 10 comprises six inlets 26 and outlet 28 which are in communication with stator and rotor assembly 30 to which is connected hub 32 having detents 34.

Figure 2:
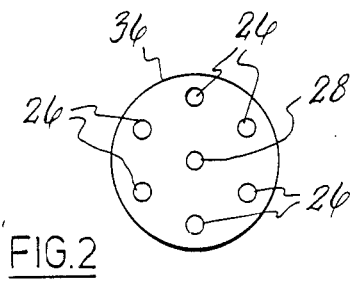
FIG. 2 is a plan view of the stator of a valve of the invention
Figure 3:
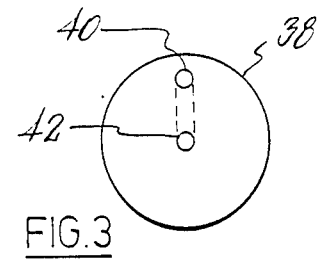
FIG. 3 is a plan view of the rotor of a valve of the invention.

FIG. 2 shows the arrangement of inlets and outlet in that face of stator 36 which abuts the face of rotor 38 shown in FIG. 3. In that face of rotor 38 which abuts the face of stator 36 shown in FIG. 2 are two interconnecting holes 40, 42 whereby hole 42 is in permanent alignment with outlet 28 and hole 40 is aligned with any one of the inlets 26. Although six inlets 26 are shown more or less can be used as desired.

In operation start switch 20 which is controlled by any suitable timing device or programme causes power to be applied to motor 12, which is in this case a 24 V A.C. motor, by closing switch SW. As soon as the motor turns, position sensor 24 rides on the outside of hub 32 thereby closing microswitch 22. This maintains the supply of power to motor 12 since start switch 20 is designed to close its switch SW only for a sufficient time to start motor 12.

Figure 4:
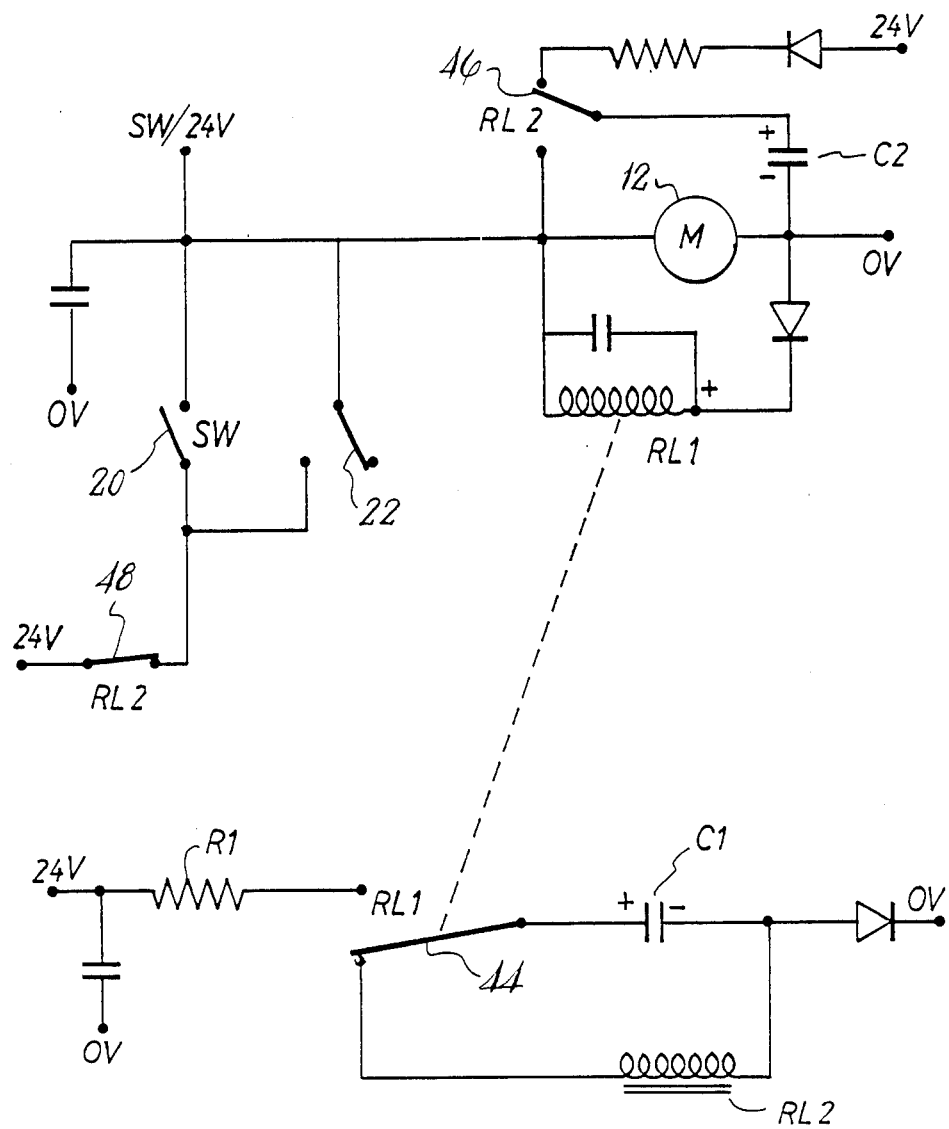
FIG. 4 is a circuit diagram of the control circuit.

The provision of power to motor 12 simultaneously causes the provision of power to relay RL1. This causes switch 44 to move from the position shown in FIG. 4 to its other position thereby charging capacitor C1. This is suitably of 220 μF capacity fed via resistor R1 which may be of 100 ohms, 0.5 watt.

As soon as hole 40 in rotor 38 is in alignment with the next one of holes 26 in stator 36, sensor 24 falls into the corresponding detent 34 in hub 32 and microswitch 22 opens thereby removing the power supply from motor 12. This immediately removes power from relay RL1 causing switch 44 to move to the position shown in FIG. 4. This activates relay RL2 by virtue of the charge on capacitor C1. This immediately causes switch 46 of relay RL2 to connect capacitor C2 across motor 12. This applies DC braking to motor 12 causing it to stop immediately and prevents any overshooting of the desired position. When the charge on capacitor C1 has drained away, relay RL2 is de-energised. Switch 46 then returns to its rest position allowing capacitor C2 to be recharged for the next operation. Capacitor C2 may be of high capacitance eg 6600 μF which is charged via resistor R2 which may be 100 ohms, 0.5 watt.

Optionally relay RL2 may have a second switch 48 which opens when relay RL2 is energised to prevent the triggering of switch 20 when braking is applied. Switch 48 closes after capacitor C1 has discharged.

The sequence may then be repeated any desired number of times at predetermined intervals dependent on the samples being analysed.

I claim:

1. A multiposition rotary liquid sampling valve having a plurality of inlets, one outlet and a rotor having means for connecting any one of the inlets to the outlet, which comprises an electric motor for turning the rotor, means for applying power to the motor, means for sensing the position of the rotor and a DC braking circuit, connected to the sensing means for immediately stopping the motor when the rotor reaches a desired position by disconnecting the power applied to the motor and simultaneously applying a braking action to the motor.

2. A sampling valve according to claim 1 in which the motor is driven at a speed of about 5 rpm via step-down gearing.

3. A sampling valve according to claim 1 in which the means for applying power to the motor comprises a timing means or programming device for switching on the power to the motor at predetermined intervals.

4. A sampling valve according to claim 1 in which the sensing means comprises a hub, mounted coaxially with the rotor, having detents in its outer surface, and a probe for detecting said detents, said probe being connected to a microswitch.

5. A sampling valve according to claim 4 in which the hub forms an integral part of the valve.

6. A sampling valve according to claim 1 in which the sensing means comprises a cam shaft fitted coaxially with the drive shaft of the motor and a probe connected to a microswitch, for detecting the position of the cam.

* * * * *